United States Patent
Endo et al.

(10) Patent No.: US 9,098,935 B2
(45) Date of Patent: Aug. 4, 2015

(54) IMAGE DISPLAYING APPARATUS, IMAGE DISPLAYING METHOD, AND COMPUTER READABLE MEDIUM FOR DISPLAYING AN IMAGE OF A MAMMARY GLAND STRUCTURE WITHOUT OVERLAPS THEREOF

(75) Inventors: Tokiko Endo, Nagoya (JP); Atsuko Sugiyama, Nasushiobara (JP); Shigeharu Ohyu, Yaita (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 765 days.

(21) Appl. No.: 11/193,477

(22) Filed: Aug. 1, 2005

(65) Prior Publication Data

US 2006/0029268 A1 Feb. 9, 2006

(30) Foreign Application Priority Data

Aug. 3, 2004 (JP) .................................. 2004-226942
Jul. 27, 2005 (JP) .................................. 2005-216587

(51) Int. Cl.
*G06K 9/00* (2006.01)
*G06T 11/00* (2006.01)
(Continued)

(52) U.S. Cl.
CPC ............... *G06T 11/008* (2013.01); *A61B 6/463* (2013.01); *A61B 6/502* (2013.01); *G06T 15/08* (2013.01)

(58) Field of Classification Search
CPC .................. G06T 11/008; G06T 15/08; G06T 2207/10112; G06T 2207/30068; A61B 6/463; A61B 6/502
See application file for complete search history.

(56) References Cited

U.S. PATENT DOCUMENTS 4,924,505 A * 5/1990 Leberl et al. .................. 382/287
5,640,956 A   6/1997 Getzinger et al.
(Continued)

FOREIGN PATENT DOCUMENTS

CN   1145675 A    3/1997
JP   4-354940     12/1992
(Continued)

OTHER PUBLICATIONS

Kita et al., "Correspondence between different view breast X-rays using a simulation of breast deformation", 1998, IEEE.*

(Continued)

*Primary Examiner* — Katrina Fujita
(74) *Attorney, Agent, or Firm* — Oblon, McClelland, Maier & Neustadt, L.L.P.

(57) ABSTRACT

Three-dimensional data is associated with a first imaging area including a left breast of a subject to be examined and a second imaging area including a right breast of the subject. An image displaying apparatus includes a specifying unit that specifies a nipple position of the left breast on the basis of positional information of pressure plates from the three-dimensional data. The image displaying apparatus also includes a generating unit that generates, by a maximum intensity projection, four projection images from the three-dimensional data. Two of the projection images respectively correspond to a plurality of divided areas of the left breast in the first imaging area divided on the basis of the specified nipple position. Two of the projection images respectively correspond to a plurality of divided areas of the right breast in the second imaging area. The four projection images are simultaneously displayed.

20 Claims, 15 Drawing Sheets

(51) Int. Cl.
*A61B 6/00* (2006.01)
*G06T 15/08* (2011.01)

(56) References Cited

U.S. PATENT DOCUMENTS

| | | | | |
|---|---|---|---|---|
| 6,574,499 | B1* | 6/2003 | Dines et al. | 600/427 |
| 7,085,406 | B2* | 8/2006 | Alyassin | 382/131 |
| 2003/0007598 | A1* | 1/2003 | Wang et al. | 378/37 |
| 2003/0169915 | A1* | 9/2003 | Takeo | 382/132 |
| 2003/0212327 | A1 | 11/2003 | Wang et al. | |
| 2005/0226375 | A1* | 10/2005 | Eberhard et al. | 378/62 |

FOREIGN PATENT DOCUMENTS

| JP | 8-186762 | 7/1996 |
|---|---|---|
| JP | 2003-531516 | 10/2003 |
| JP | 2003-334183 | 11/2003 |

OTHER PUBLICATIONS

Alyassin, A., "Automatic transfer function generation for volume rendering of high-resolution x-ray 3D digital mammography images", 2002, Proc. SPIE 4681, Medical Imaging 2002: Visualization, Image-Guided Procedures, and Display, 338-348.*

Office Action issued Nov. 30, 2010, in Japan Patent Application No. 2005-216587 (with English translation).

* cited by examiner

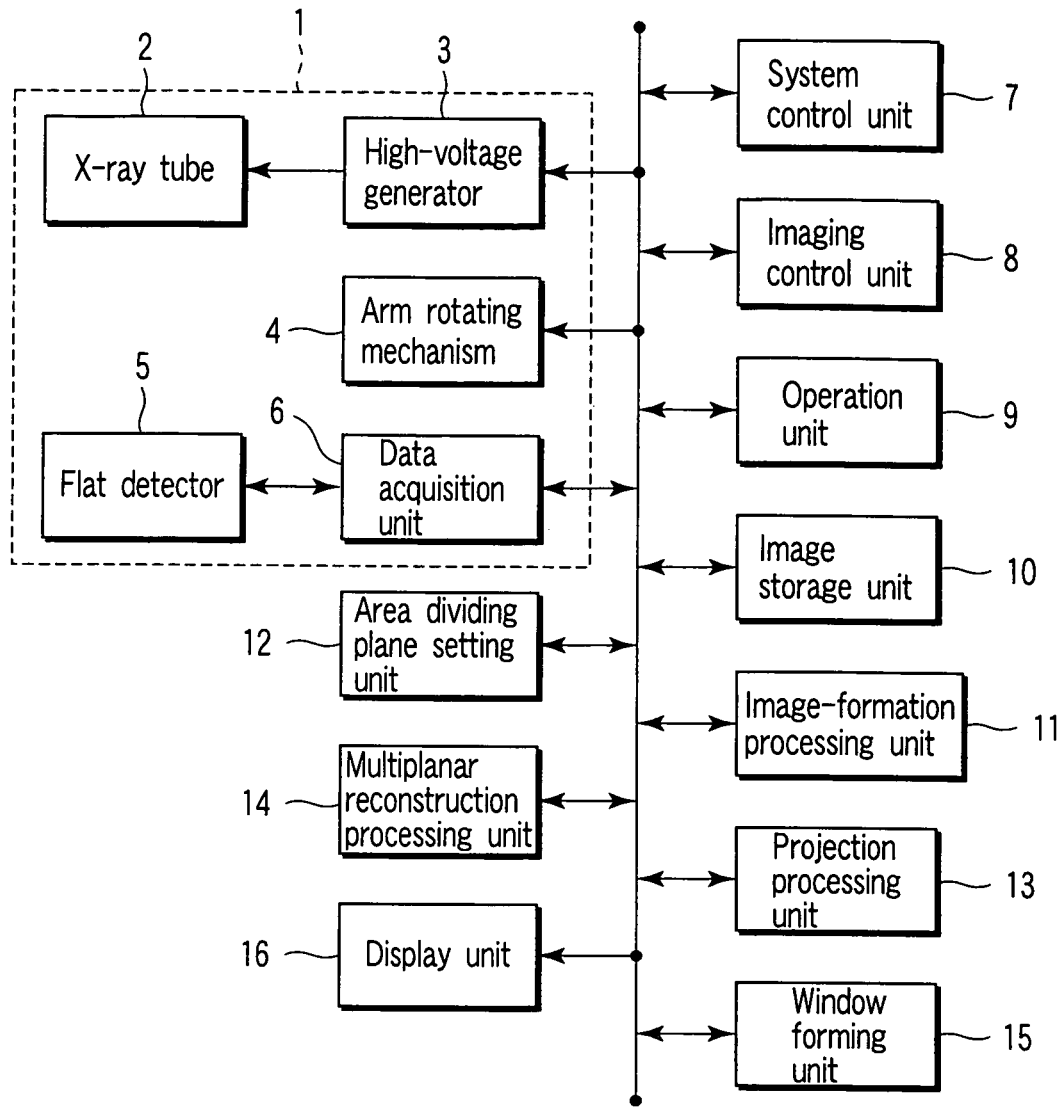
F I G. 1

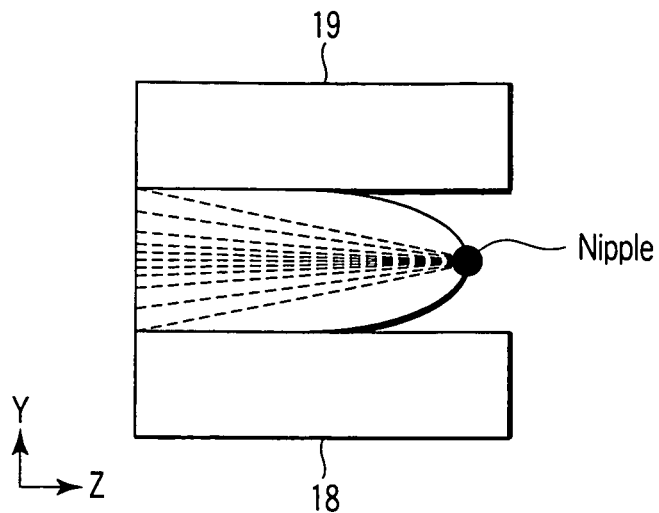
F I G. 11
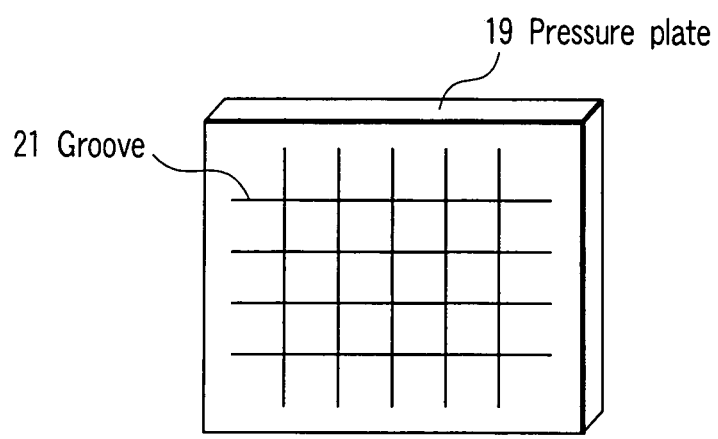
F I G. 12

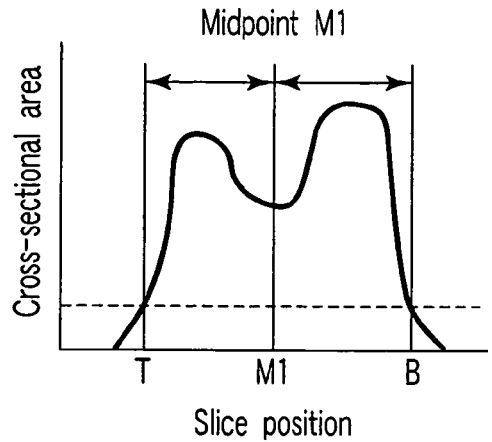 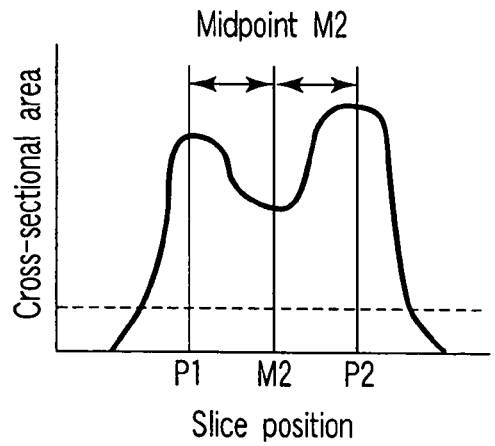
FIG. 15A  FIG. 15B
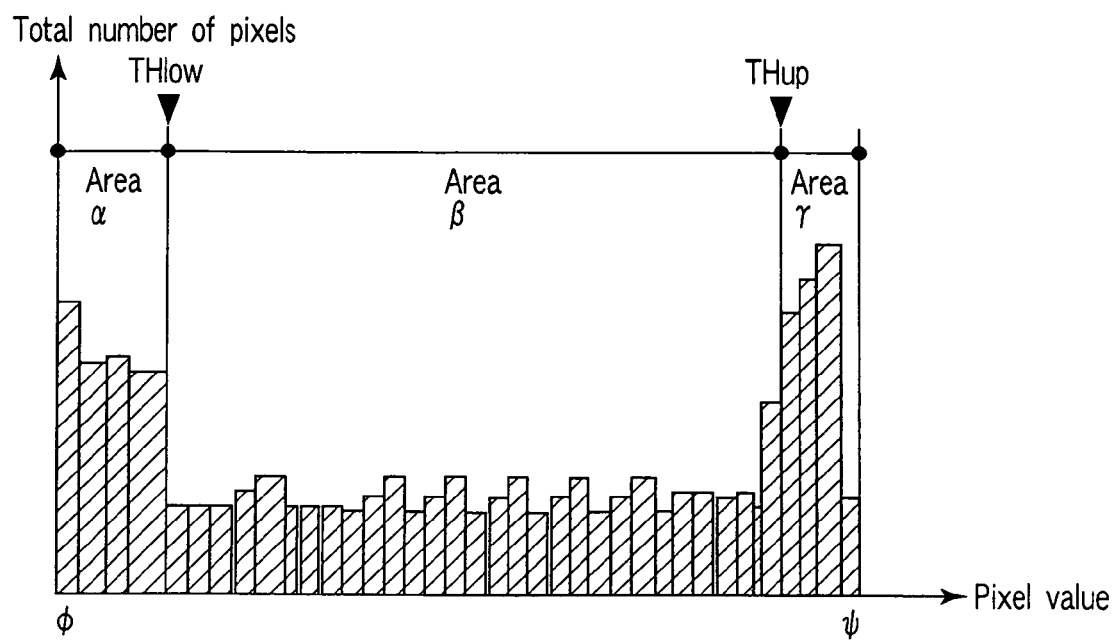
FIG. 16 a: Breast in which almost all mammary gland layers are replaced by fat layers b: Inhomogeneous high-density breast c: Breast with high mammary gland density

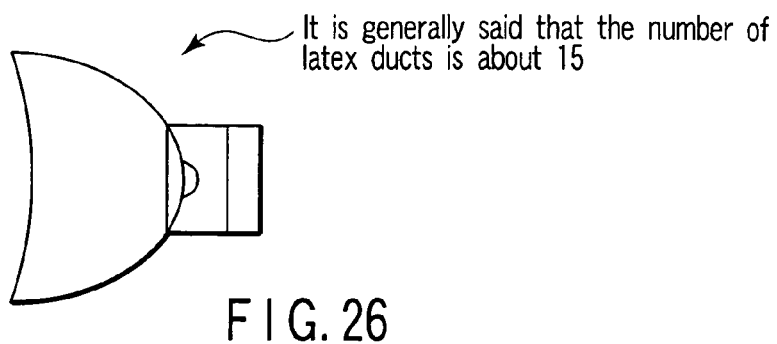

FIG. 26

| Body posture | Imaging method | Inclination angle of pressure plate | Method of generating divided images | Codes corresponding to structure of breast |
|---|---|---|---|---|
| Sitting position | Cephalocaudal direction imaging | -20 to 20° | Method A | Upper surface |
| Sitting position | Cephalocaudal direction imaging | -20 to 20° | Method B | Lower surface |
| Sitting position | External/internal oblique imaging | -80 to -20° | Method A | Outside |
| Sitting position | External/internal oblique imaging | -80 to -20° | Method B | Inside |
| Sitting position | External/internal side imaging | -100 to -80° | Method A | Outside |
| Sitting position | External/internal side imaging | -100 to -80° | Method B | Inside |
| Sitting position | External/internal oblique imaging | 20 to 80° | Method A | Inside |
| Sitting position | External/internal oblique imaging | 20 to 80° | Method B | Outside |
| Sitting position | External/internal side imaging | 80 to 100° | Method A | Inside |
| Sitting position | External/internal side imaging | 80 to 100° | Method B | Outside |
| Lateral position | External/internal side imaging | -20 to 20° | Method A | Outside |
| Lateral position | External/internal side imaging | -20 to 20° | Method B | Inside |
| ⋮ | ⋮ | ⋮ | ⋮ | ⋮ |

FIG. 27

IMAGE DISPLAYING APPARATUS, IMAGE DISPLAYING METHOD, AND COMPUTER READABLE MEDIUM FOR DISPLAYING AN IMAGE OF A MAMMARY GLAND STRUCTURE WITHOUT OVERLAPS THEREOF

CROSS-REFERENCE TO RELATED APPLICATIONS

This application is based upon and claims the benefit of priority from prior Japanese Patent Applications No. 2004-226942, filed Aug. 3, 2004; No. 2005-216587, filed Jul. 27, 2005, the entire contents of both of which are incorporated herein by reference.

BACKGROUND OF THE INVENTION

1. Field of the Invention

The present invention relates to an image displaying apparatus, image displaying method, computer readable medium, and computer program product which display an image associated with the breast pressed between pressure plates in the form of a slab.

2. Description of the Related Art

As a conventional technique for imaging the breasts, mammographic radiography for acquiring two-dimensional images from one direction upon spreading mammary glands by pressing the breasts is available. The mammary glands in the breasts have three-dimensional structures comprising small clusters like grapes. If, therefore, mammary glands are imaged as they are, each mammary gland overlaps another. This makes it impossible to make detailed evaluation. For this reason, the breasts have been elongated by being clamped to reduce the overlaps of mammary glands and image them using smaller amounts of X-rays (reference: Tao Wu and 10 others, "Tomographic mammography using a limited number of low-dose conebeam projection images", Medical Physics, Vol. 30, No. 3, published by American association of Physicists in Medicine, March 2003, pp. 365-380).

At the time of imaging, however, mammary glands on the front side of the tube overlap mammary glands on the detector side to make it difficult to discriminate/diagnose a tumor.

BRIEF SUMMARY OF THE INVENTION

It is an object of the present invention to provide an image displaying apparatus, image displaying method, computer readable medium, and computer program product which display an image which allows easy comprehension of a mammary gland structure by eliminating overlaps of mammary glands.

According to a first aspect of the present invention, there is provided an image displaying apparatus comprising means for storing data associated with an imaging area including a breast of a subject to be examined, means for generating, from the data, a plurality of images respectively corresponding to a plurality of divided areas in the imaging area divided on the basis of positional information of pressure plates, and means for displaying the generated image.

According to a second aspect of the present invention, there is provided an image displaying apparatus which generates an image of a breast, comprising means for generating a plurality of partial area images of the image, and display means for displaying all the generated partial area images on one window, and also displaying codes of partial areas associated with a breast structure.

According to a third aspect of the present invention, there is provided an image displaying apparatus which generates an image of a breast, comprising means for calculating an area dividing position, means for generating an image of a divided area divided at the area dividing position, and means for displaying the generated image, wherein the means for calculating the area dividing position detects positional information of a nipple of the breast on the basis of the image and calculates the area dividing position on the basis of positional information of the detected nipple.

According to a fourth aspect of the present invention, there is provided an image displaying apparatus which generates an image of a breast, comprising means for calculating an area dividing position, means for generating an image of a divided area divided at the calculated area dividing position, and means for displaying the generated image, wherein the calculating means extracts a schematic internal structure of a breast on the basis of the image, and calculates a dividing position on the basis of a position of the schematic structure.

According to a fifth aspect of the present invention, there is provided an image displaying method comprising a step of generating, from data associated with an imaging area including a breast of a subject to be examined, a plurality of images respectively corresponding to a plurality of divided areas in the imaging area divided on the basis of positional information of a pressure plate, and a step of displaying the generated image.

According to a sixth aspect of the present invention, there is provided a computer readable medium which records a computer program product for causing a computer to realize means for generating, from data associated with an imaging area including a breast of a subject to be examined, a plurality of images respectively corresponding to a plurality of divided areas in the imaging area divided on the basis of positional information of a pressure plate, and means for displaying the generated image.

According to a seventh aspect of the present invention, there is provided a computer program product for causing a computer to realize means for generating, from data associated with an imaging area including a breast of a subject to be examined, a plurality of images respectively corresponding to a plurality of divided areas in the imaging area divided on the basis of positional information of a pressure plate, and means for displaying the generated image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a view showing the arrangement of an X-ray mammography apparatus according to an embodiment of the present invention;

FIG. 11 is a view for supplementary explanation of an area dividing plane (nipple plane) determination processing by image processing by the area dividing plane setting unit in FIG. 1;

FIG. 12 is a view showing an example of grooves formed in the surface of a pressure plate in this embodiment;

FIGS. 15A and 15B are views for supplementary explanation of dividing plane setting in the area dividing plane setting unit 12 in FIG. 1;

FIG. 16 is a view for supplementary explanation of threshold determination processing in the area dividing plane setting unit 12 in FIG. 1;

FIG. 26 is a view for supplementary explanation of latex duct tracking processing in the area dividing plane setting unit 12 in FIG. 1; and FIG. 27 is a view showing the correspondence relationship between an imaging method or the like and a dividing method in this embodiment.

DETAILED DESCRIPTION OF THE INVENTION

An embodiment of the present invention will be described below with reference to the views of the accompanying drawing. According to this embodiment, the present invention can be provided as an X-ray three-dimensional imaging apparatus as an X-ray diagnostic apparatus, an image displaying apparatus incorporated in the X-ray three-dimensional imaging apparatus, an image displaying method, a computer program product for causing a computer to realize a combination of means for image display, and a computer readable medium which records the computer program product.

Figure 4A:
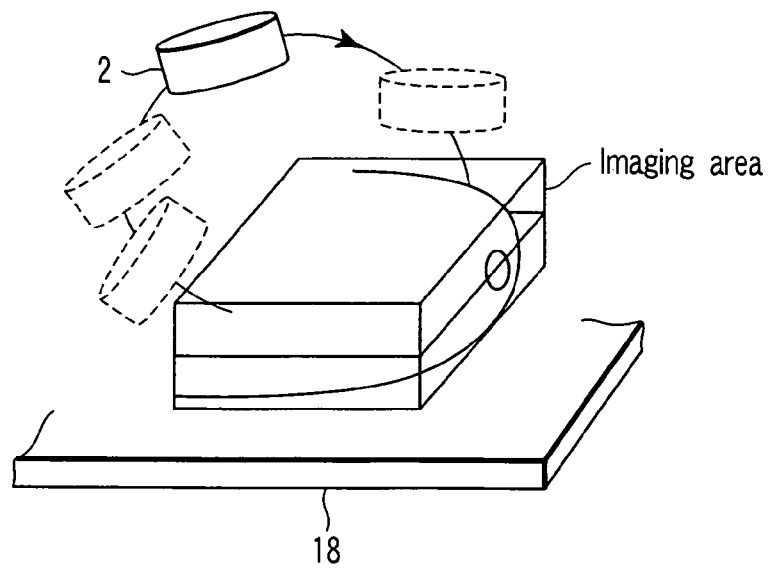
FIGS. 4A and 4B are views showing the movement of an X-ray tube at the time of X-ray imaging in this embodiment.
Figure 4B:
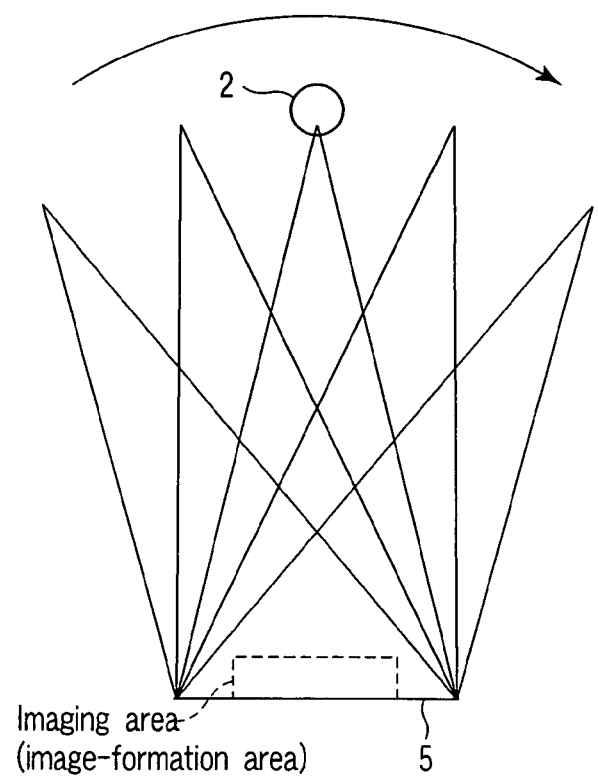

This embodiment uses an X-ray three-dimensional imaging method. According to the X-ray three-dimensional imaging method, a tomographic image is reconstructed from a plurality of X-ray transmission images obtained by imaging from many directions (this operation will be referred to as "image formation" hereinafter to discriminate it from "reconstruction" in X-ray CT). In actual processing, a plurality of rays passing through points (pixels) on a designated slice are selected from a plurality of X-ray transmission images obtained by imaging from a plurality of directions, and pixel values corresponding to the selected rays are selected and added. In principle, this processing makes a region on a designated slice sharp and makes a region at a position outside the slice blur. In such an X-ray three-dimensional imaging method, a tomographic image can be formed in an area where X-ray cones in all imaging directions are superimposed (see FIGS. 4 and 5).

Figure 3:
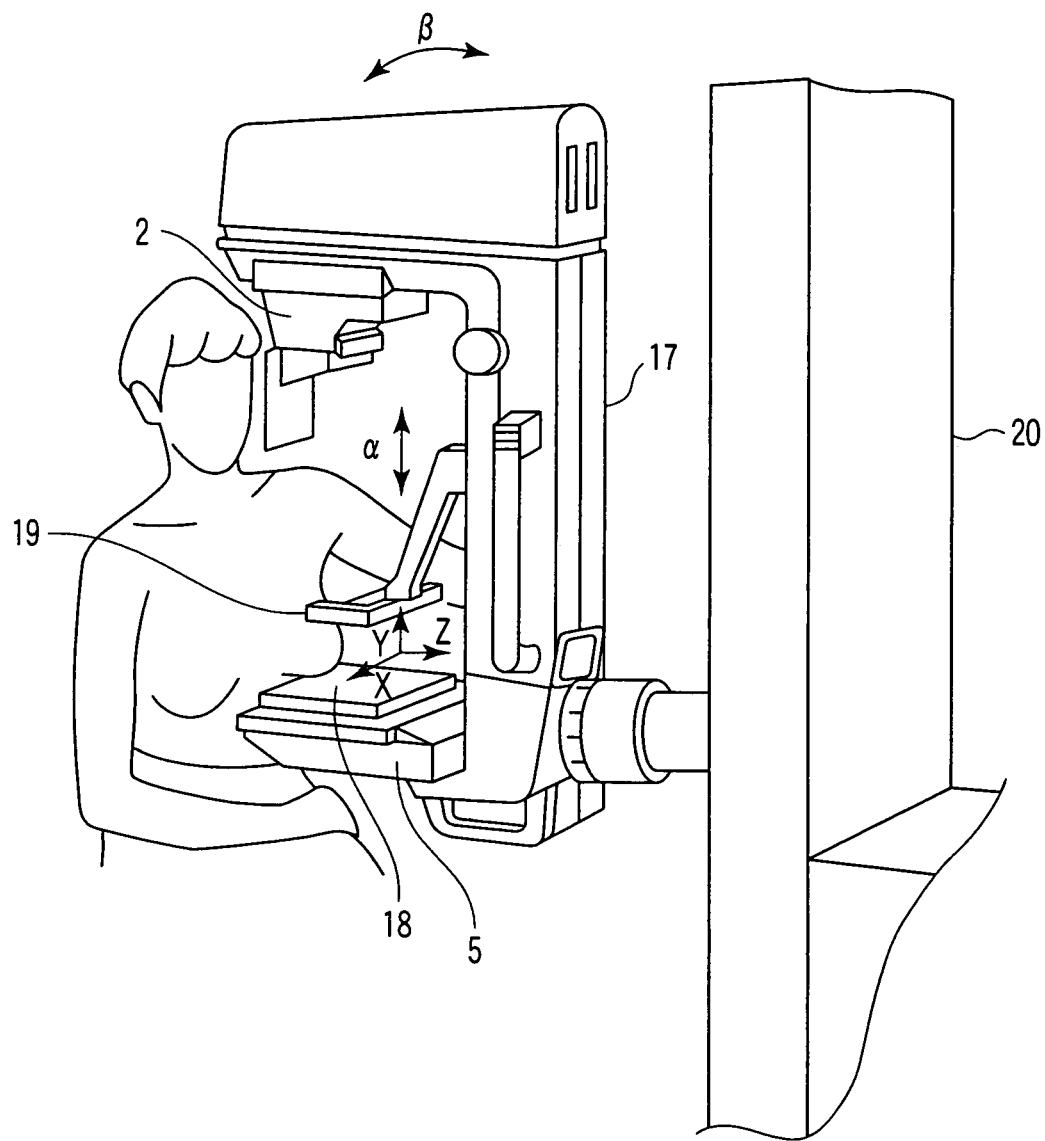
FIG. 3 is a perspective view showing the structure of the main part of the X-ray imaging table of the X-ray mammography apparatus in FIG. 1.

FIG. 1 shows the arrangement of an X-ray mammography apparatus according to an embodiment of the present invention. The X-ray mammography apparatus includes an X-ray imaging table 1. As shown in FIG. 3, the X-ray imaging table 1 is designed such that an X-ray tube 2 is mounted on one end of a C-arm 17. The X-ray tube 2 generates X-rays upon receiving a high voltage from a high-voltage generator 3. A flat detector (also called a flat panel detector) 5 is mounted on the other end of the C-arm 17 so as to face the X-ray tube 2. The flat detector 5 has a plurality of semiconductor detection elements of a direct conversion type designed to directly convert incident X-rays into electrical signals or an indirect conversion type designed to convert incident X-rays into light through phosphors and convert the light into electrical signals. A plurality of semiconductor detection elements are arrayed in the form of a two-dimensional lattice. The signal charges generated by the plurality of semiconductor detection elements upon application of X-rays are read as digital signals through a data acquisition unit 6. The flat detector 5 can be replaced by a combination of an image intensifier and an optical camera.

The flat detector 5 is housed in a lower pressure plate 18 fixed to the C-arm 17. The lower pressure plate 18 is provided to press the breast of the subject together with an upper pressure plate 19 supported on the C-arm 17 so as to be movable with respect to an arrow α. The C-arm 17 is supported on the arm rotating mechanism 4 mounted in a column 20 so as to be swingably movable with respect to an arrow β. For example, the rotational center axis of the C-arm 17 is set near the lower pressure plate 18, and the lower pressure plate 18 is rotated in a direction opposite to the C-arm 17, thereby causing the X-ray tube 2 to swingably move in multi-directional imaging while stopping the lower pressure plate 18 on which the breast of the subject is placed.

Figure 6:
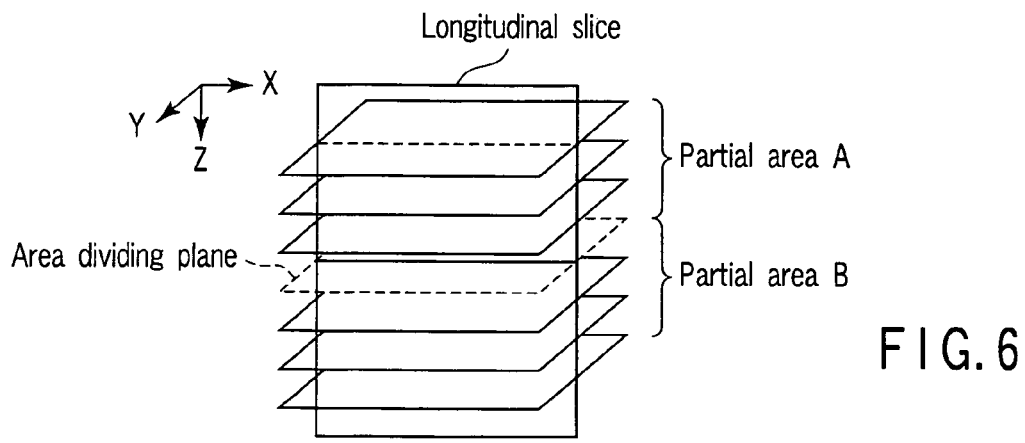
FIG. 6 is a view for supplementary explanation of the generation of a partial projection image by a projection processing unit in FIG. 1.

In addition to the X-ray imaging table 1, the X-ray mammography apparatus according to this embodiment includes a system control unit 7, imaging control unit 8, operation unit 9, image storage unit 10, image-formation processing unit 11, area dividing plane setting unit 12, projection processing unit 13, multiplanar reconstruction processing unit 14, window forming unit 15, and display unit 16. The imaging control unit 8 controls the high-voltage generator 3, arm rotating mechanism 4, and data acquisition unit 6 in accordance with the imaging conditions set in advance to execute multi-direction imaging (three-dimensional imaging) with respect to the breast of the subject which is pressed between the pressure plates 18 and 19 in the form of a slab (see FIGS. 4A and 4B). Three-dimensional imaging is performed with respect to each of the right and left breasts, and the data of a plurality of X-ray transmission images associated with the right breast in different imaging directions and the data of a plurality of X-ray transmission images associated with the left breast in different imaging directions are stored in the image storage unit 10. As shown in FIG. 6, the image-formation processing unit 11 forms a plurality of tomographic images corresponding to a plurality of slices set at equal intervals within a substantially rectangular parallelepiped image-formation area (to be abbreviated to an imaging area) defined by X-ray fluxes and the pair of pressure plates 18 and 19. A set of tomographic images will be referred to a volume image or simply as a volume. The data of a plurality of tomographic images, i.e., the data of a volume image, is stored in the image storage unit 10.

The area dividing plane setting unit 12 sets an area dividing plane for dividing an imaging area into a plurality of partial areas, typically two partial areas in the thickness direction (Y-axis direction). Although an area dividing plane can be arbitrarily set by manually operating the operation unit 9, its initial position is automatically set by the area dividing plane setting unit 12. An initial area dividing plane is selected from three types of planes. Selecting operation is performed in advance or during processing.

Figure 7:
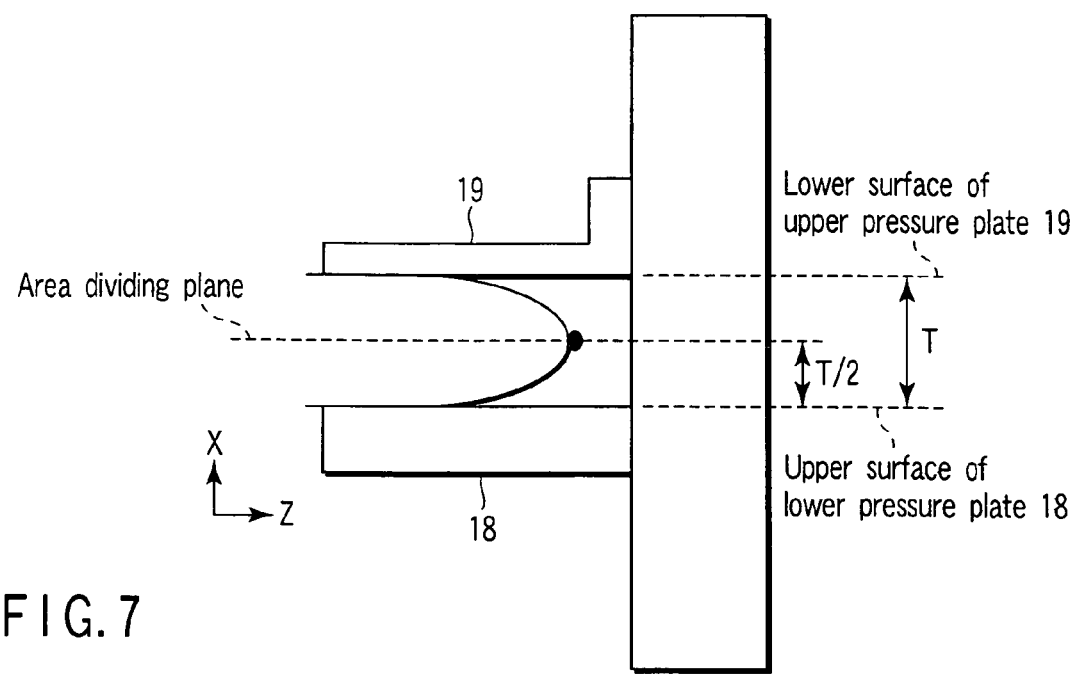
FIG. 7 is a view showing an area dividing plane (middle plane) in FIG. 6.
Figure 8:
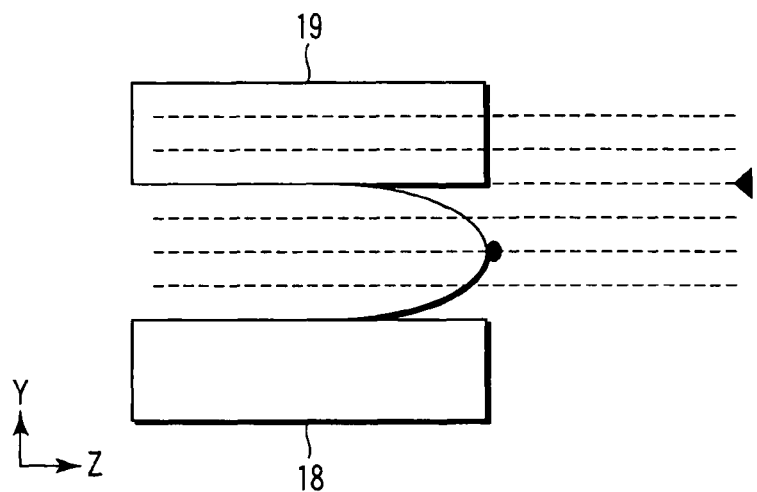
FIG. 8 is a view for supplementary explanation of area dividing plane (middle plane) determination processing by image processing by an area dividing plane setting unit in FIG. 1.

As shown in FIG. 7, the first area dividing plane is a middle plane between the two upper and lower pressure plates 18 and 19 which sandwich the breast. More specifically, letting T be the distance between the upper surface of the lower pressure plate 18 and the lower surface of the upper pressure plate 19 (the thickness of the pressed breast), the first area dividing plane is set at a plane (middle plane) which is parallel to the pressure plates 18 and 19 and located at a distance of T/2 from the upper surface of the lower pressure plate 18. Since the lower pressure plate 18 is fixed on the C-arm 17, if the lower surface position of the upper pressure plate 19 is specified, a middle plane can be set. The lower surface position of the upper pressure plate 19 can be detected by a position sensor such as a rotary encoder. Alternatively, the lower surface position of the upper pressure plate 19 can be specified by image processing. Since the lower surface position of the upper pressure plate 19 is at the boundary between the pressed breast and the upper pressure plate 19, the lower surface position can be specified by extracting a slice at which a tomographic image changes from a soft tissue image to a homogeneous image of the pressure plate 19 from a plurality of nearby slices, as shown in FIG. 8.

In this case, as shown in FIG. 12, if very shallow and thin grooves 21 are formed in the surface of each of the pressure plates 18 and 19 in advance, the surface positions of the pressure plates 18 and 19 can be easily specified from generated volume image data. Since the pattern of the formed grooves 21 is known, an index indicating how much the pattern is included in a two-dimensional image can be calculated by pattern matching. Such an index is checked for each slice image of formed images. A slice with the highest index corresponds to the surface position of the pressure plate 19. Forming different patterns of grooves on the upper and lower pressure plates 18 and 19 makes it possible to separately determine the surfaces of the upper and lower pressure plates. In places of the grooves 21, markers which do not transmit X-rays may be formed on the pressure plates 18 and 19.

Figure 9:
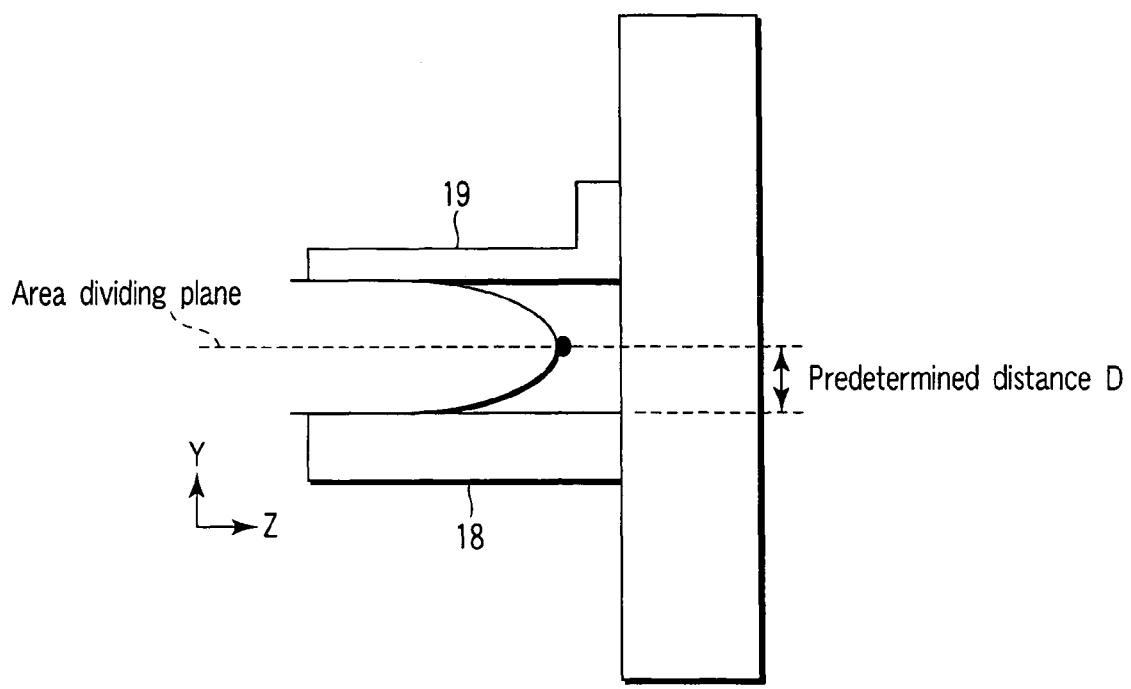
FIG. 9 is a view showing the area dividing plane (predetermined plane) in FIG. 6.
Figure 10A:
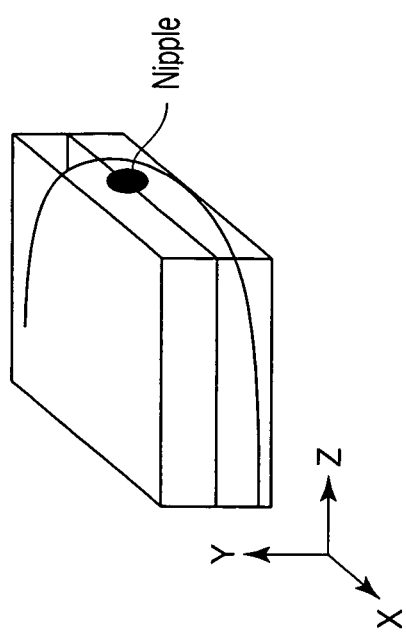
FIGS. 10A to 10D are views showing the area dividing plane (nipple plane) in FIG. 6.
Figure 10D:
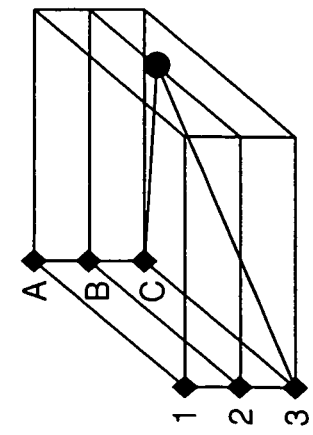
Figure 10C:
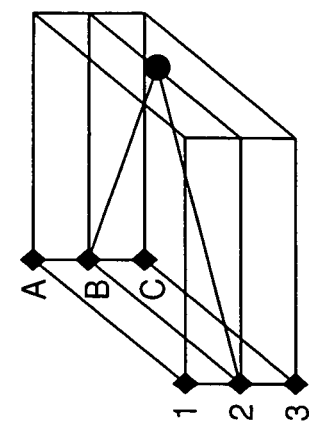
Figure 10B:
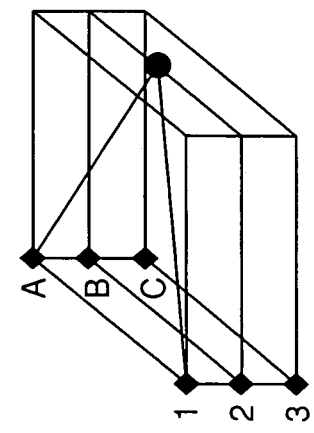

As shown in FIG. 9, the second area dividing plane is set at a plane spaced apart from the upper surface of the lower pressure plate 18 of the two upper and lower pressure plates 18 and 19 which sandwich the breast by a predetermined distance D. As described above, the lower pressure plate 18 is fixed on the C-arm 17, and hence is always set at a predetermined position regardless of the lower surface position of the upper pressure plate 19.

The position of the lower or upper pressure plate 18 or 19 is specified as follows. Assume that each slice of a volume image is almost parallel to the pressure plates 18 and 19. Since the direction of each slice is determined by image-formation processing conditions, slices like those described above can be easily generated.

Let N be the number of slices of a volume image, z1 be the position of the first slice, z2 be the position of the last slice, and z3 be the surface of the lower or upper pressure plate 18 or 19. The values z1 and z2 are designated as conditions for image formation. The value z3 may be either a constant for apparatus design or the value measured by a sensor. Alternatively, this value may be the value specified from an image as described above.

When an area dividing plane is designated to be located at a position spaced apart from the surface of the pressure plate 18 or 19 by a distance L in the z-axis direction, the position of the area dividing plane is at the slice position represented by $$a = 1 + N(z3 + L - z1)/(z2 - z1)$$

In general, this value is not an integer and represents that the area dividing plane exists between the maximum integer which does not exceed a and the minimum integer which is larger than a.

As shown in FIGS. 10 and 11, of a plurality of planes which can be extracted from a tomographic image with high precision by threshold processing and pattern matching processing, pass through the nipple, and are parallel or oblique to the pressure plates 18 and 19, a plane exhibiting the highest integral value of pixel values within each plane is selected, and the third area dividing plane is set at the selected plane. Note that a plane passing through the barycenter of pixel values within the imaging area may be set as the third area dividing plane in place of the plane passing through the nipple.

Nipple extraction processing will be described in detail later.

The imaging area is divided by an area dividing plane into a partial area (A) which is substantially the upper half on the upper pressure plate 19 side and a partial area (B) which is substantially the lower half on the lower pressure plate 18 side. The projection processing unit 13 generates a projection image corresponding to the partial area of substantially the upper half from a plurality of tomographic images within the partial area of substantially the upper half by maximum intensity projection (MIP). The projection processing unit 13 generates a projection image corresponding to the partial area of substantially the lower half from a plurality of tomographic images within the partial area of substantially the lower half by maximum intensity projection. As is well known, in MIP processing, a plane parallel to the pressure plates 18 and 19 is set as a projection plane, and the maximum value of pixel values on an axis (ray) perpendicular to the projection plane is regarded as the value of an intersection pixel between the ray and the projection plane. That is, projection processing is separately performed for each partial area in the thickness direction of the pressed breast. Projection processing is not limited to MIP and may be processing for integrating pixel values on a ray. The projection processing unit 13 generates a partial projection image of the partial area of substantially the upper half and a partial projection image of the partial area of substantially the lower half of each of the left and right breasts, and also generates a projection image of the entire imaging area of each of the left and right breasts. The data of the partial projection images of the partial areas of substantially the upper and lower halves of each of the left and right breasts and the data of the projection image of the entire imaging area of each of the left and right breast are stored in the image storage unit 10.

The multiplanar reconstruction processing unit 14 generates, from a plurality of tomographic images within an imaging area, a tomographic image of a longitudinal slice shown in FIG. 6 which is perpendicular to the slices and passes through the middles of the slices, for each of the left and right breasts. The data of the longitudinal tomographic images of the right and left breast are stored in the image storage unit 10.

Figure 2:
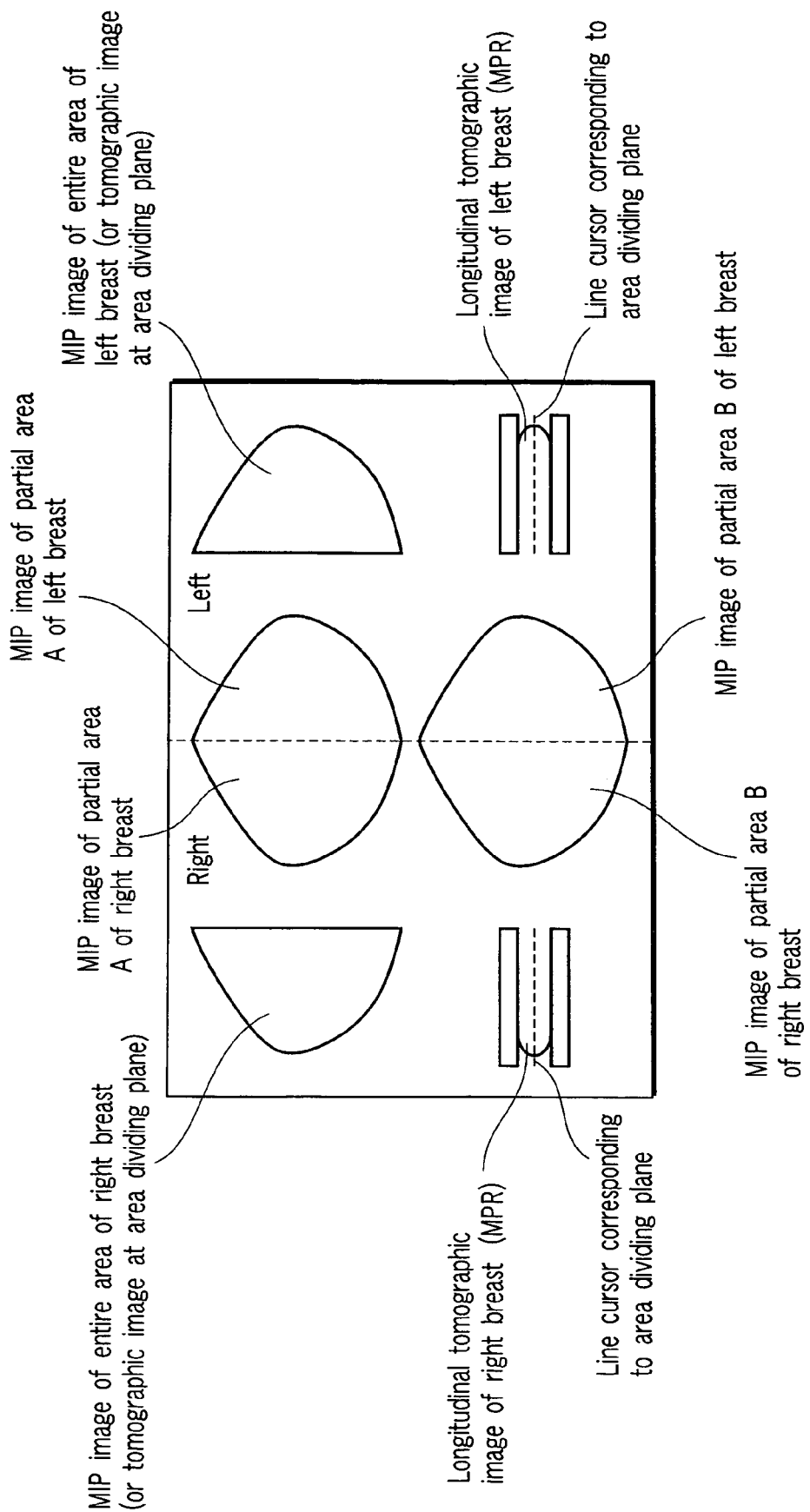
FIG. 2 is a view showing an example of a display window displayed on a display unit in FIG. 1.

The window forming unit 15 forms a display window on the display unit 16. As shown in FIG. 2, the partial projection image of substantially the upper half of the right breast and the partial projection image of substantially the upper half of the left breast are symmetrically arranged about the midline of the window which is indicated by the dotted line. The partial projection image of substantially the lower half of the right breast and the partial projection image of substantially the lower half of the left breast are symmetrically arranged about the midline of the window below the partial projection images of substantially the upper halves. The projection image of the entire area of the right breast and the projection image of the entire area of the left breast are symmetrically arranged about the midline of the window outside the partial projection images of substantially the upper halves. Note that the projection images of the entire areas of the left and right breasts can be switched to the tomographic images concerning the area dividing planes which are generated by the multiplanar reconstruction processing unit 14. The longitudinal tomographic image of the right breast and the longitudinal tomographic image of the left breast are symmetrically arranged about the midline of the window outside the partial projection images of substantially the lower halves. A line cursor corresponding to the area dividing plane is superimposed on each longitudinal tomographic image. The display position of each line cursor can be vertically moved in accordance with proper operation of the operation unit 9. When the line cursor is moved, the partial projection image is updated following the movement.

Note that FIG. 27 shows the structures of the breast and an imaging methods and displaying methods which correspond to the structures.

Referring to FIG. 27, "outside" and "inside" are codes corresponding to the structures of the breast. A volume area is divided into two areas on the basis of a dividing plane, and images of the respective areas are generated. In this case, a method of generating an obverse-side area of the dividing plane is defined as method A, and a method of generating the reverse-side area of the dividing plane is defined as method B. Codes corresponding to methods A and B can be determined from a table like that shown in FIG. 27.

As described above, according to this embodiment, images are formed by dividing a volume image (multi-slice tomographic image) of the pressed breast, and the obverse—and reverse-side images are displayed. As a method of determining an area dividing plane for dividing operation, for example, a method of determining a middle slice between the pressure plates as an area dividing plane or a method of determining an area dividing plane by extracting a fat layer by image processing is used. In general X-ray mammography, since a plurality of mammary glands overlap each other, such an overlap may be mistakenly diagnosed as a tumor. In contrast, according to the present invention, forming breast-divided images makes it possible to provide an image without any overlaps of mammary glands and improve the diagnosis precision.

Note that the third area dividing plane described above is a plane passing through the nipple. Nipple extraction processing by the area dividing plane setting unit 12 will be described below.

Figure 13:
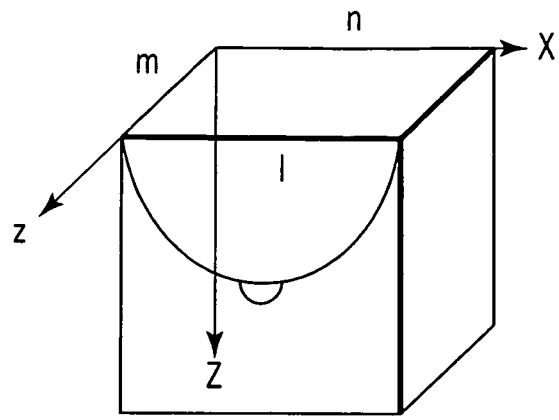
FIG. 13 is a view for supplementary explanation of nipple extraction processing in an area dividing plane setting unit 12 in FIG. 1.

As shown FIG. 13, three axes of volume data are represented by X, Y, and Z. Assume that the volume data has sizes n, m, and l [pixel] in the X, Y, and Z directions, respectively. Scattering image noise (speckle noise or the like) is removed from the volume data by filtering. The filtered volume data is then binarized by threshold processing. A threshold is set to a proper value in advance to discriminate an air area from the other area mainly including the breast and nipple. For example, "1" is assigned to a voxel having a value exceeding the threshold, i.e., a voxel in the area including the breast and nipple, and "0" is assigned to a voxel having a value equal to or less than the threshold, i.e., a voxel in the air area.

Assume that a vector f is a vector indicating a direction in which the probability of the presence of the nipple increases. The inner product of the vector f and each voxel assigned "1" is calculated. A voxel exhibiting the largest inner product is selected from a plurality of voxels assigned "1". The coordinate value of the center of the selected voxel is specified as a nipple position.

As another nipple extraction method, a semi-automatic method is available. First of all, the operator manually designates a nipple position on a two-dimensional image such as a projection display image or MIP display image (maximum value projection image) generated from volume data. In this designation stage, only a position on the two-dimensional window is determined. A position in the depth direction (projection direction) must be specified.

The operator searches for pixel values along a projection straight line (typically a direction perpendicular to the window) passing through the point designated by the operator on the two-dimensional image, and determines a nipple position by either of the following methods (a) and (b).

(a) A voxel having the largest pixel value is selected from a plurality of voxels on a projection straight line, and the position of the selected voxel is set as a nipple position.

(b) Voxels each having a pixel value exceeding a predetermined threshold are extracted from a plurality voxels on a projection straight line. The middle position of an area (voxel train) where the extracted voxels are continuous is set as a nipple position. If there are a plurality of voxel trains, the longest voxel train is selected. Note that a threshold can be determined from, for example, MIP display conditions (gray-level and window width).

According to another nipple extraction method, the operator designates a nipple position on an arbitrary slice generated by MPR (multiplanar reconstruction processing) from volume data. The designated position is set as a nipple position.

According to still another nipple extraction method, the operator designates a nipple position on an image displayed by Volume Rendering. The three-dimensional coordinates of the nipple are determined from the designated position as follows. Search is made for opacities used for Volume Rendering along a projection straight line passing through a point clicked on the Volume Rendering image. Opacities each equal to or more than the first threshold are accumulated. A point whose cumulative value exceeds the second threshold is set as a nipple position.

Still another nipple extraction method is an image processing method of automatically calculating a nipple position by performing image processing for each slice of MPR image display. This image processing method mainly includes two types of image processing methods. The first method is a method of performing pattern matching (Pattern Matching Algorithm) with a two-dimensional mask for discriminating the shape of a nipple. The second image processing method is performed as follows. First of all, scattering image noise (speckle noise or the like) is removed from volume data by filtering. The filtered volume data is then binarized on the basis of pixel values. A threshold used for binarization is the same as that used for separating an air area from the other area including the breast and the like, as described above. Filtering of, e.g., first derivative and second derivative is performed for the binarized volume data to extract a contour. The extracted contour line is then adjusted.

Figure 14:
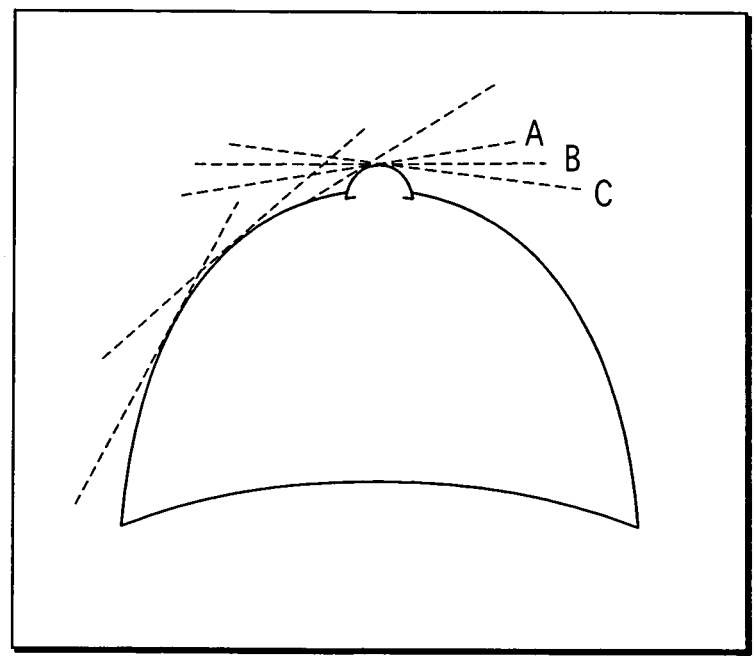
FIG. 14 is a view for supplementary explanation of another nipple extraction processing in the area dividing plane setting unit 12 in FIG. 1.

As exemplified in FIG. 14, the slope of a tangent to each of multiple points on the contour line is obtained, and a nipple position is calculated by using the tangent position of a tangent B whose slope is 0, i.e., a tangent which typically becomes almost parallel to the body axis of the subject. Alternatively, a position at which the differential value becomes maximum is set as a nipple position.

In still another nipple extraction method, first of all, high-frequency component filtering is performed for the volume data of the breast to remove spatial high-frequency components contained in the volume data. The volume data is binarized into an air area and the other area including the breast and nipple by threshold processing. If necessary, as padding processing, dilation with a small distance is performed with respect to the other area ("1" area) including the breast and nipple, other than the air area, and then erosion with the same distance is performed.

Erosion is performed for the "1" area of volume data A, which has undergone padding processing, by a distance n1, and dilation is performed for the resultant data by a distance n2. In this case, n2 is equal to or more than n1. The volume data having undergone this processing will be referred to volume data B. This operation has an effect of smoothing the surface of the "1" area. As a consequence, volume data B corresponds to volume data A from which projections are removed. When volume data B from which projections are removed is subtracted from volume data A having projections, volume data C in which a plurality of projection areas are left is generated. One of a plurality of projection areas in volume data C is a nipple area.

Connected areas in volume data c are labeled (this operation will be referred to as connected component labeling). The volumes and barycenter coordinate values of the respective areas are obtained. One of the areas is then selected on the basis of selection conditions set in advance for each of imaging methods (several standard methods of pressing breasts). For example, an area in which the inner product of a barycenter coordinate value and the vector f is the largest is selected from areas each of which has a volume equal to or more than V1 and equal to or less than V2. The vector f is a vector indicating a direction in which the probability of the presence of a nipple increases. The barycenter of the selected area is obtained as a nipple position.

Figure 5:
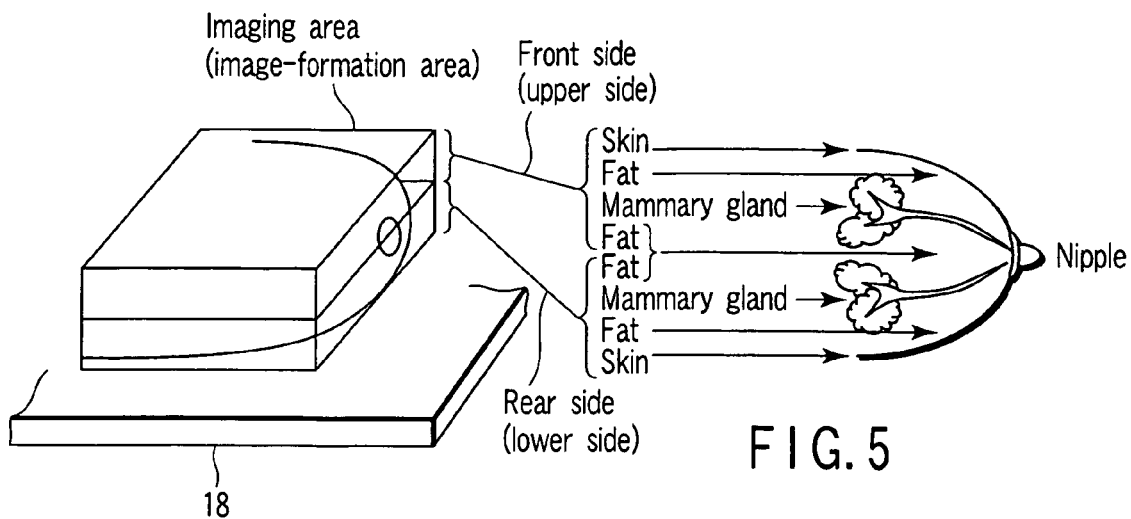
FIG. 5 is a view showing an image-formation area (imaging area) based on an image-formation processing unit in FIG. 1.

The area dividing plane setting unit 12 has a function of specifying a dividing plane from a change in the distribution of mammary gland areas. Referring to FIG. 5, the middle plane which separates two mammary gland areas is set as a dividing plane. A method of extracting mammary glands from volume data will be described first. On an X-ray tomographic image, a mammary gland area has a larger pixel value than many other structures of the breast. If, therefore, a given threshold is determined, mammary gland areas can be roughly obtained by binarization processing. A method of determining a threshold will be described later. A plurality of slice planes almost parallel to the pressure plates 18 and 19 are set within an imaging area. In other words, slice planes (XZ planes) are set at predetermined intervals in the thickness direction of the pressed breast. The cross-sectional area of an extracted mammary gland area is obtained for each slice plane. When a cross-sectional area is obtained for each slice position, a graph showing changes in the cross-sectional areas of the mammary gland areas in the thickness direction is obtained, as shown in FIG. 15A. On this graph, a range (a range from a point T to a point B) having an area larger than a predetermined area (broken line) is obtained, and a midpoint M1 of this range is set as a specific slice position.

According to another method, as shown in FIG. 15B, a slice position P1 below the midpoint M1 is obtained, at which the cross-sectional area becomes a peak value. Likewise, a peak value above M1 is obtained, and a slice position P2 corresponding to the peak value is specified. That is, P2 is determined. The midpoint between P1 and P2 is represented by M2.

The slice position (M1 or M2) obtained in this manner is set as a dividing plane. In this case, a plurality of slices, i.e., T, P1, M1, P2, and B, are determined, projection images can be generated and displayed upon area division into a plurality of areas by these slices as dividing planes.

Note that a threshold can be obtained from display conditions for image display such as MIP and MPR set by the operator. In this case, the following arrangement is preferable. A threshold extracted by a determined threshold is superimposed/displayed (in, for example, red) on an image such as a MIP or MPR image. When a display condition is changed, a threshold is determined again in accordance with the operation by the operator, and an area is extracted again, thereby updating the superimposed image. In addition, several automatic methods of determining a threshold are known, e.g., the Optimal threshold method, Otsu's method, and percentile method, and one of these methods may be used.

Another threshold determining method in the setting unit 12 will be described. First of all, the setting unit 12 generates a histogram of pixel values from volume data (see FIG. 16). An area other than the breast is determined from the histogram. This area is represented by α. Areas in the breast are represented by β and γ according to the histogram. In this case, the values of black and white portions in FIG. 16 are represented by φ and ϕ, respectively (φ<ϕ).

area α: corresponding to the fat layer of the breast
area β: not corresponding to the main structure of the breast
area γ: corresponding to the mammary gland area of the breast The pixel value of a background (air) area is smaller than φ and is not shown in the histogram of FIG. 16.

A binary image is generated by setting different values for the areas α, β, and γ, and a mammary gland structure is extracted.

Figure 17A:
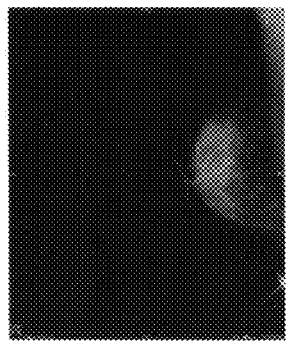
FIGS. 17A, 17B, and 17C are images for supplementary explanation of mammary gland area extraction processing in the area dividing plane setting unit 12 FIG. 1.
Figure 17B:
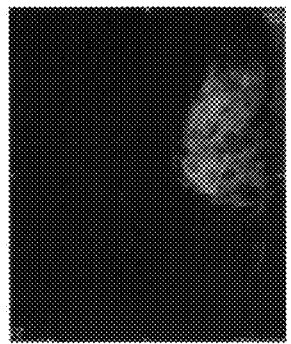
Figure 17C:
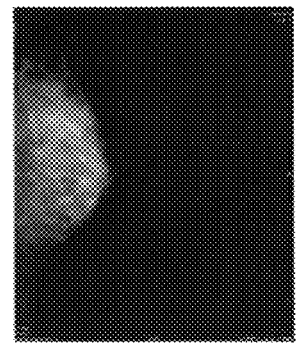

A threshold is then determined. In general, in the breast, the mammary gland structure has three states. The states depend on age, lactational history, and the like:

state a: the breast in which all the mammary gland layers are replaced by the fat layers (see FIG. 17A)

state b: the state of the inhomogeneous high-density breast (see FIG. 17B)

state c: the breast with high mammary gland density (see FIG. 17C)

Figure 18:
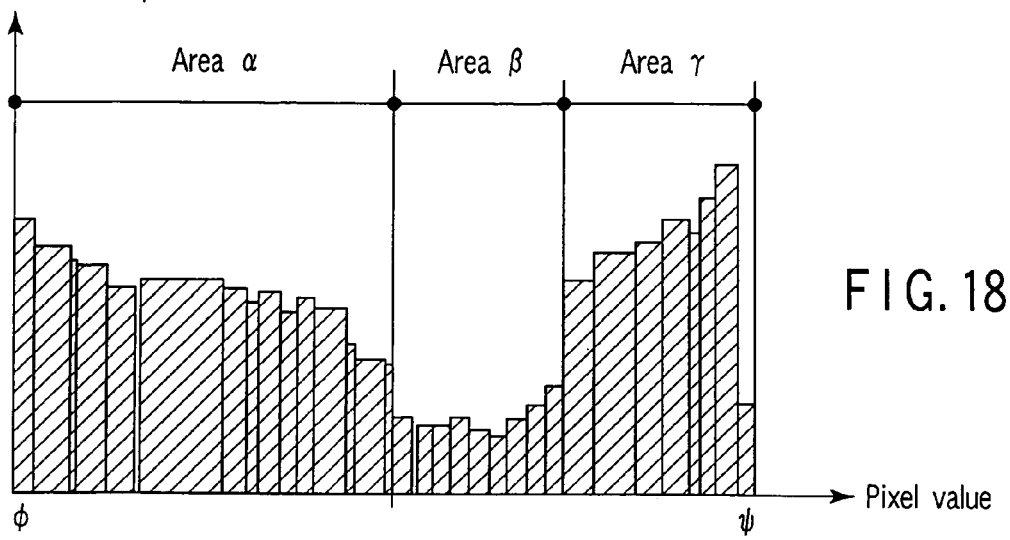
FIG. 18 is a view showing a histogram associated with the volume data of the breast in a state wherein the mammary gland layer is replaced by the fat layer.

In this case, consideration is given to that the breast has three states. FIG. 18 exemplifies the histogram for the breast in which all the mammary gland layers are replaced by the fat layers. In the breast in which all the mammary gland layers are replaced by the fat layers, the mammary gland structure area y can be easily divided into a mammary gland area and a non-mammary gland area according to the histogram.

Figure 19:
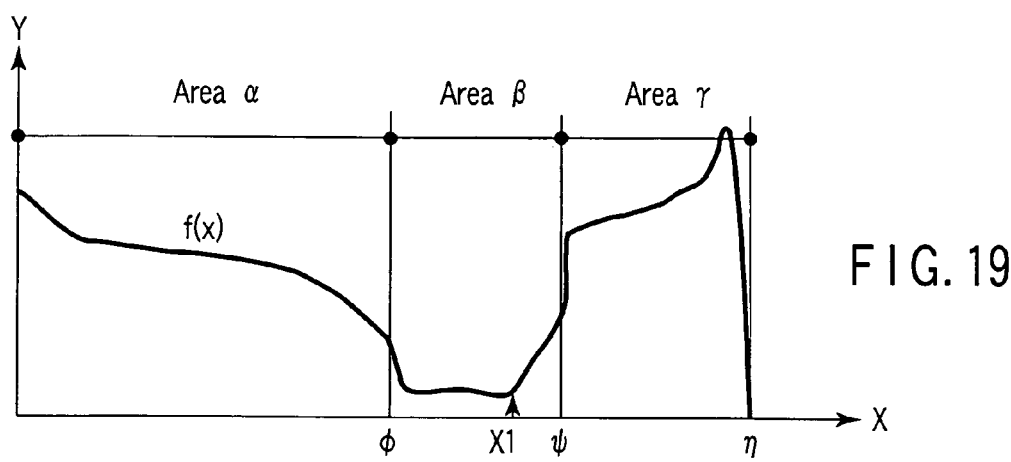
FIG. 19 is a view for supplementary explanation of curve approximation processing for a histogram in mammary gland area extraction processing in FIG. 18.

Letting X be a pixel value and Y be the total number of pixels, a histogram can be expressed by an approximate curve f(x) as shown in FIG. 19.

The operator designates a boundary position φ between the areas α and β, and a boundary position φ between the areas β an γ. X with which the differential value of Y=f(X) changes from minus to plus is set to X1 (n is an integer). The area β is the area which is centered on X1 and corresponds to ε % of a pixel width η. Note that ε is either set by the operator, or a default value of ε is set in advance by using the histogram of a model.

Figure 20:
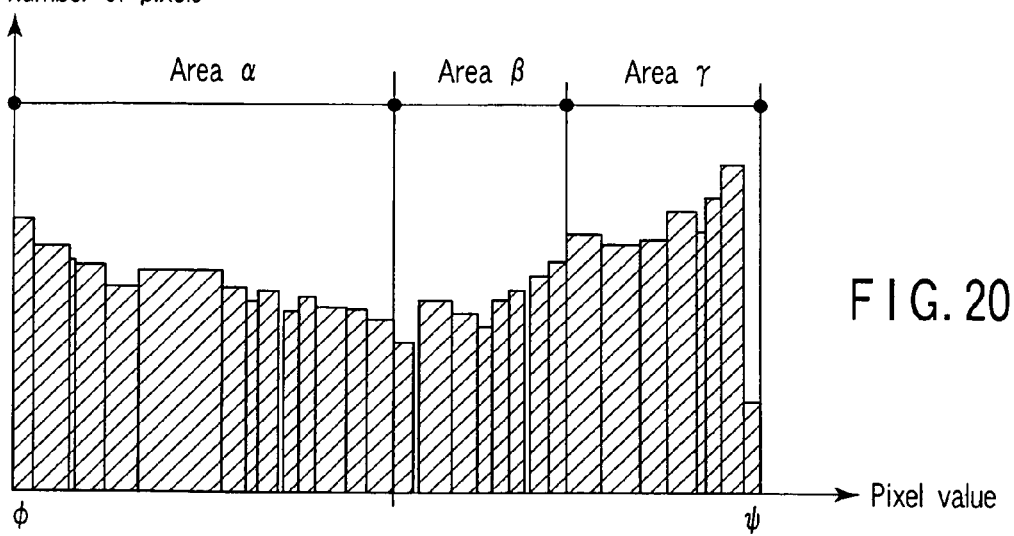
FIG. 20 is a view showing a histogram associated with the volume data of the inhomogeneous high-density breast.
Figure 21:
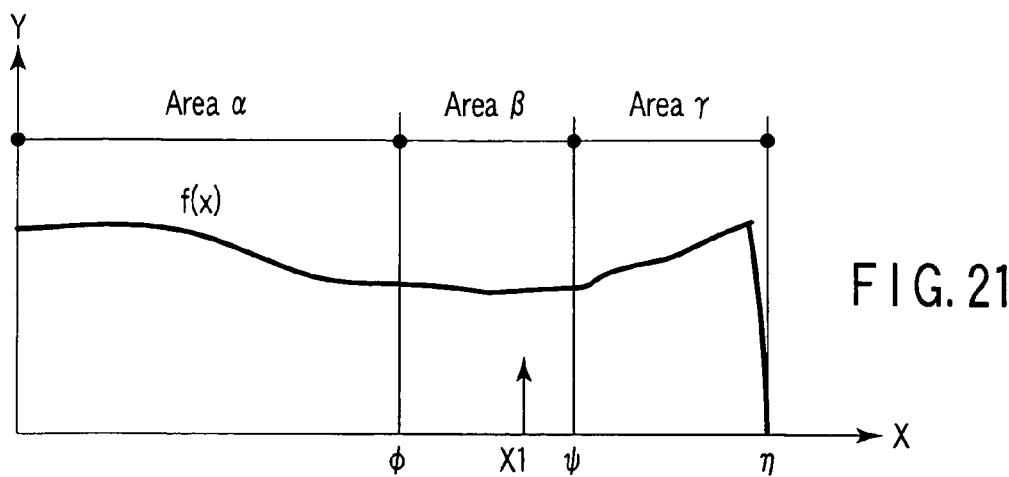
FIG. 21 is a view for supplementary explanation of curve approximation processing for a histogram in mammary gland area extraction processing in FIG. 20.

FIG. 20 exemplifies the histogram of the inhomogeneous high-density breast. Letting X be a pixel value and Y be the total number of pixels, a histogram can be expressed by using an approximate curve f(X) as shown in FIG. 21. However, no conspicuous change is seen.

Figure 22:
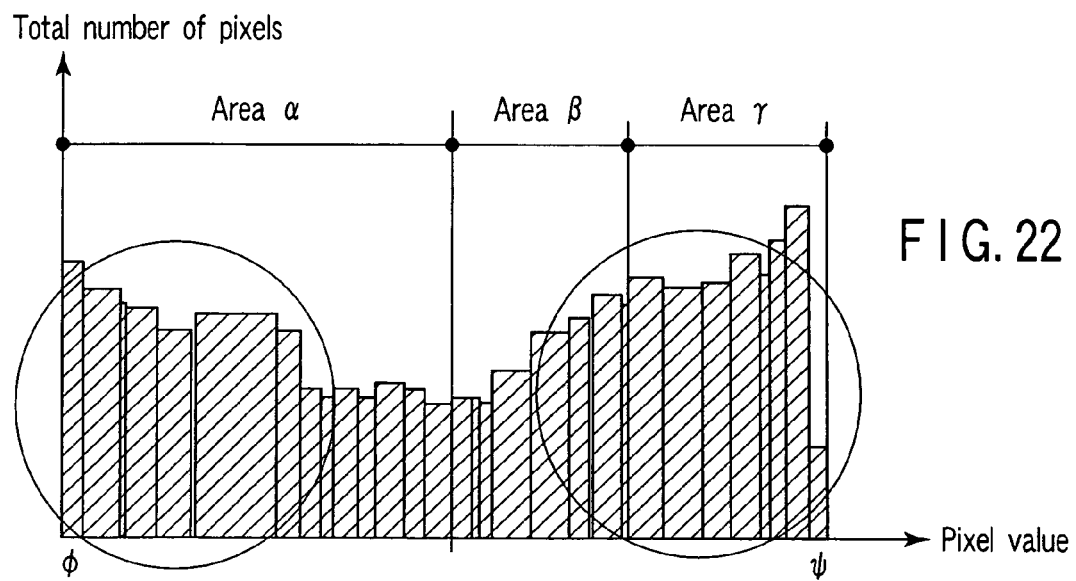
FIG. 22 is a view showing a histogram associated with volume data having undergone edge enhancement processing.

In this case, the image is converted into frequency area information through Fourier transform, and the low-frequency areas are lowered in the frequency space, thereby enhancing edges. This information is restored to the real space by inverse Fourier transform. In the histogram after frequency processing, edge enhancement is done as shown in FIG. 22.

When a histogram is approximated by an approximate curve f(X) with X and Y representing a pixel value and the total number of pixels, respectively, an edge-enhanced histogram is obtained. On the edge-enhanced histogram, the operator manually designates the boundary position φ between the areas α and β, and the boundary position φ.

Figure 23:
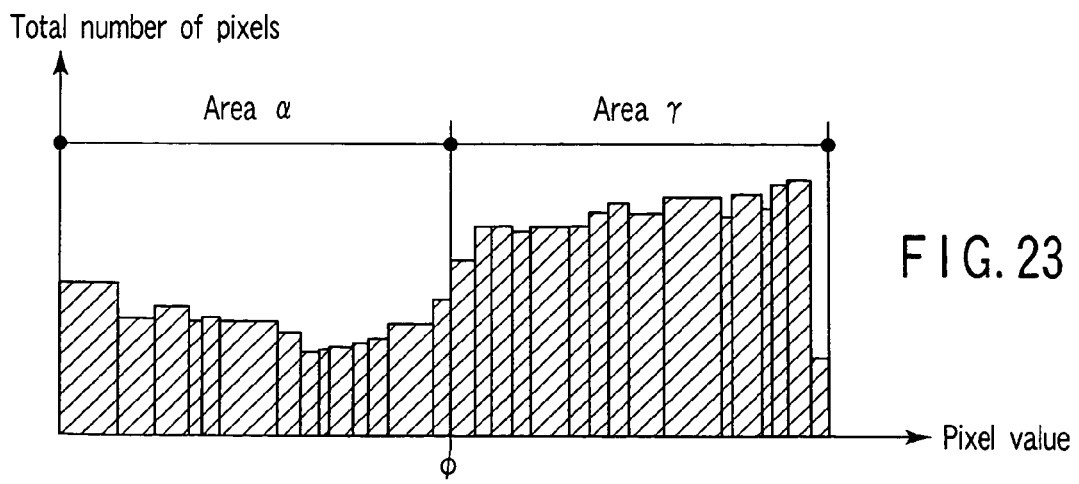
FIG. 23 is a view showing a histogram associated with volume data in a state wherein a mammary gland density is high.

The most area of the breast with a high mammary gland density is a mammary gland area, as shown in FIG. 23. The operator designates the boundary position φ between the areas α and γ.

There is also available a method of setting a threshold for a histogram by determining a pixel value threshold as a default in advance and selecting the type of breast. The operator selects, as a presented image, one of the breast in which all the mammary gland layers are replaced by the fat layers, the inhomogeneous high-density breast, and the breast with a high mammary gland density. A threshold corresponding to each breast image is determined in advance, and threshold processing is performed by using such a value.

There are also available a method of automatically determining, as a presented image, one of the breast in which all the mammary gland layers are replaced by the fat layers, the inhomogeneous high-density breast, and the breast with a high mammary gland density, and a threshold setting method to be used after the selection. First of all, as a presented image, one of the breast in which all the mammary gland layers are replaced by the fat layers, the inhomogeneous high-density breast, and the breast with a high mammary gland density is selected in accordance with the correlation values obtained by calculating correlations with modeled histograms.

A threshold is determined for each breast image in advance. Threshold processing is performed by using a threshold for the type of selected breast as a default (reference).

Figure 24:
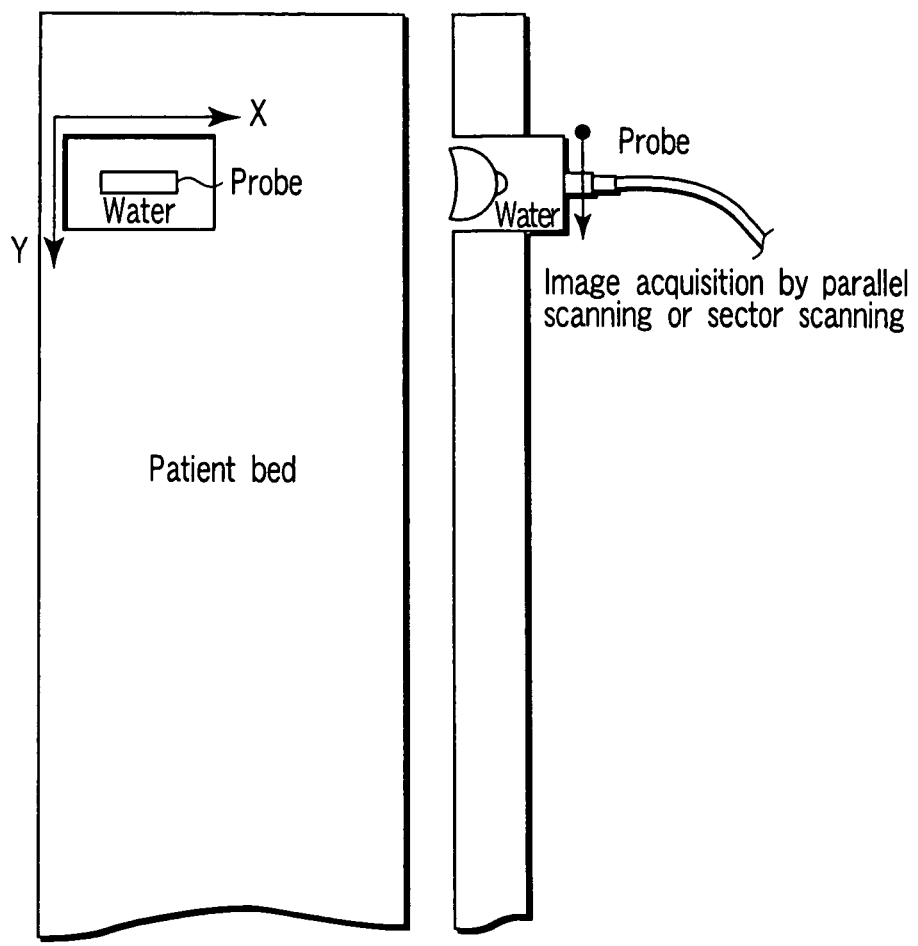
FIG. 24 is a view showing an outline of an apparatus for scanning a mammary gland area with ultrasound waves in this embodiment.

A method of setting a dividing plane from volume data will be described next. As shown in FIG. 24, according to this technique, a dividing plane is semi-automatically set from the volume data of the breast which is acquired by ultrasound scanning. First of all, the operator who is to perform imaging operation designates a slice (can be plural) passing through the nipple or to be divisionally displayed. The operator then performs 3D scanning with respect to an area including the breast by ultrasound waves to acquire volume data. An image is displayed upon using the set plane as a dividing plane.

Figure 25:
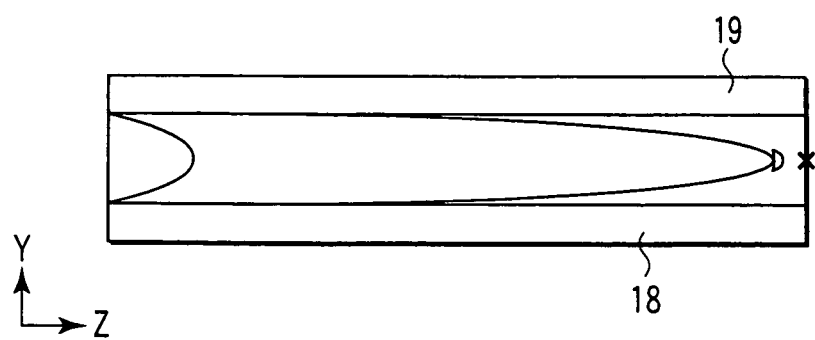
FIG. 25 is a view for supplementary explanation of positioning processing for the nipple and a marker in the area dividing plane setting unit 12 in FIG. 1.

Alternatively, a dividing plane may be set from volume data in the following manner. This is a method of mechanically setting a slice by acquiring the volume data of an area including the breast using a jig which can perform positioning to make the relationship between the nipple position and the image position be easily understood. As shown in FIG. 25, one of a marker and the nipple is positioned to the other.

Image data is acquired, and a dividing plane passing through the nipple is set. For example, a dividing plane is set by using the distance from the pressure plate 18 or 19. The operator sets a dividing plane by rotating the plane about the nipple (marker) as the rotation center.

Another method of extracting a mammary gland structure from volume data will be described. According to this technique, the operator selects a tracking start point, and extracts a mammary gland structure from the start point by using a general tracking method. Volume data is displayed as a two-dimensional image (a projection, MIP, or MPR image). As shown in FIG. 26, the operator clicks the position of a latex duct. The latex duct is then tracked by using a known blood vessel tracking method.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image displaying apparatus, comprising:
 a memory configured to store three-dimensional data associated with a first imaging area including a left breast of a subject to be examined, the three-dimensional data also associated with a second imaging area including a right breast of the subject, the left breast and the right breast being pressed between pressure plates;
 at least one processing circuit configured to implement
  a specifying unit configured to specify a nipple position of the left breast on the three-dimensional data based on positional information of the pressure plates, and
  a generating unit configured to generate at least a left upper half image, a left lower half image, a right upper half image, and a right lower half image, the left upper half image being a projection image corresponding to an entire upper half area of the first imaging area of the three-dimensional data based on the specified nipple position of the left breast, the left lower half image being a projection image corresponding to an entire lower half area of the first imaging area of the three-dimensional data based on the specified nipple position of the left breast, the right upper half image being a projection image corresponding to an entire upper half area of the second imaging area of the three-dimensional data based on a nipple position of the right breast, and the right lower half image being a projection image corresponding to an entire lower half area of the second imaging area of the three-dimensional data based on the nipple position of the right breast; and a display configured to simultaneously display the left upper half image, the left lower half image, the right upper half image, and the right lower half image.

2. The image displaying apparatus according to claim 1, wherein the at least one processing circuit is further configured to implement a determining unit configured to determine a position of one of the pressure plates, and to calculate a middle position for a division on the basis of the determined position of the one of the pressure plates.

3. The image displaying apparatus according to claim 2, wherein the determining unit includes a detecting unit configured to detect a boundary between one of the pressure plates and the left breast from one of the left upper half and left lower half images on the basis of an image of the left breast.

4. The image displaying apparatus according to claim 2, wherein the determining unit comprises a sensor which detects the position of the one of the pressure plates.

5. The image displaying apparatus according to claim 1, wherein the at least one processing circuit is further configured to implement a receiving unit configured to receive a positional relationship between one of the pressure plates and a position for a division; and a calculating unit configured to calculate an area dividing position on the basis of the position of the one of the pressure plates and the received positional relationship.

6. The image displaying apparatus according to claim 1, wherein grooves are formed in a surface of one of the pressure plates in a form of a lattice.

7. The image displaying apparatus according to claim 1, wherein the at least one processing circuit is further configured to implement a dividing plane setting unit which sets a dividing plane for dividing the second imaging area into a plurality of divided areas at a plane passing through the nipple position of the right breast.

8. The image displaying apparatus according to claim 7, wherein the dividing plane setting unit specifies the nipple position of the right breast on the basis of a result of a threshold processing for data associated with the second imaging area.

9. The image displaying apparatus according to claim 7, wherein the dividing plane setting unit specifies the nipple position of the right breast on the basis of a change in a tangential direction with respect to a contour of the right breast.

10. The image displaying apparatus according to claim 1, wherein the at least one processing circuit is further configured to implement a dividing plane setting unit which sets a dividing plane for dividing the second imaging area into a plurality of divided areas at a boundary between a plurality of mammary gland areas.

11. The image displaying apparatus according to claim 10, wherein the dividing plane setting unit specifies the boundary between the mammary gland areas on the basis of a change in a cross-sectional area of a mammary gland area concerning a thickness direction of a pressed breast.

12. The image displaying apparatus according to claim 11, wherein the dividing plane setting unit extracts the mammary gland area from data associated with the second imaging area by a threshold processing.

13. The image displaying apparatus according to claim 12, wherein the dividing plane setting unit determines a threshold from a shape of a histogram representing a relationship between a pixel value associated with the data of the second imaging area and a number of pixels.

14. The image displaying apparatus according to claim 12, wherein the dividing plane setting unit sets, as a threshold, a value designated by an operator instruction on a histogram representing a relationship between a pixel value associated with the data of the second imaging area and a number of pixels.

15. The image displaying apparatus according to claim 12, wherein the dividing plane setting unit executes an edge enhancement processing for the data of the second imaging area.

16. The image displaying apparatus according to claim 1, wherein the specifying unit is further configured to specify the nipple position of the right breast on the basis of positional information of pressure plates from the three-dimensional data associated with the second imaging area, and the right upper half image and the right lower half image are formed by dividing the second imaging area on the basis of the specified nipple position of the right breast.

17. An image displaying apparatus which generates an image of a breast, comprising:

a memory configured to store three-dimensional data associated with an imaging area of the breast; and circuitry configured to calculate an area dividing position;

generate an image of a divided area of the breast divided at the area dividing position, the image of the divided area being a projection image corresponding to an entire upper or lower area of the imaging area of the three-dimensional data based on the area dividing position; and output the generated image for display, wherein the circuitry detects positional information of a nipple of the breast on the basis of the image and calculates the area dividing position on the basis of positional information of the detected nipple.

18. An image displaying apparatus which generates an image of a breast, comprising:

a memory configured to store three-dimensional data associated with an imaging area of the breast; and circuitry configured to calculate an area dividing position;

generate an image of a divided area of the breast divided at the calculated area dividing position, the image of the divided area being a projection image corresponding to an entire upper or lower area of the imaging area of the three-dimensional data based on the area dividing position; and output for display the generated image, wherein the circuitry extracts a schematic internal structure of the breast on the basis of the image, and calculates the dividing position on the basis of a position of the schematic structure.

19. An image displaying method for an image displaying apparatus, the image displaying method comprising:

specifying a nipple position of a left breast of a subject on three-dimensional data based on positional information of pressure plates, the three-dimensional data associated with a first imaging area including the left breast, the three-dimensional data also associated with a second imaging area including a right breast of the subject;

generating, with circuitry of the image displaying apparatus, at least a left upper half image, a left lower half image, a right upper half image, and a right lower half image, the left upper half image being a projection image corresponding to an entire upper half area of the first imaging area of the three-dimensional data based on the specified nipple position of the left breast, the left lower half image being a projection image corresponding to an entire lower half area of the first imaging area of the three-dimensional data based on the specified nipple position of the left breast, the right upper half image being a projection image corresponding to an entire upper half area of the second imaging area of the three-dimensional data based on a nipple position of the right breast, and the right lower half image being a projection image corresponding to an entire lower half area of the second imaging area of the three-dimensional data based on the nipple position of the right breast; and displaying, with a display of the image displaying apparatus, the left upper half image, the left lower half image, the right upper half image, and the right lower half image.

20. A computer readable, non-transitory storage medium which stores program instructions which when executed by a computer results in a performance of steps comprising:

specifying a nipple position of a left breast of a subject on three-dimensional data based on positional information of pressure plates, the three-dimensional data associated with a first imaging area including the left breast, the three-dimensional data also associated with a second imaging area including a right breast of the subject;

generating at least a left upper half image, a left lower half image, a right upper half image, and a right lower half image, the left upper half image being a projection image corresponding to an entire upper half area of the first imaging area of the three-dimensional data based on the specified nipple position of the left breast, the left lower half image being a projection image corresponding to an entire lower half area of the first imaging area of the three-dimensional data based on the specified nipple position of the left breast, the right upper half image being a projection image corresponding to an entire upper half area of the second imaging area of the three-dimensional data based on a nipple position of the right breast, and the right lower half image being a projection image corresponding to an entire lower half area of the second imaging area of the three-dimensional data based on the nipple position of the right breast; and displaying the left upper half image, the left lower half image, the right upper half image, and the right lower half image.

* * * * *